(12) United States Patent
Tenerz et al.

(10) Patent No.: US 6,993,974 B2
(45) Date of Patent: Feb. 7, 2006

(54) SENSOR AND GUIDE WIRE ASSEMBLY

(75) Inventors: Lars Tenerz, Uppsala (SE); Mattias Tullberg, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 12 days.

(21) Appl. No.: 10/611,661

(22) Filed: Jul. 2, 2003

(65) Prior Publication Data

US 2005/0000294 A1 Jan. 6, 2005

(51) Int. Cl.
*G01L 7/00* (2006.01)
(52) U.S. Cl. .......................... 73/727; 73/756
(58) Field of Classification Search ........... 600/486, 600/488; 73/754
See application file for complete search history.

(56) References Cited

U.S. PATENT DOCUMENTS

| 3,946,724 | A | 3/1976 | La Balme |
|---|---|---|---|
| 4,685,469 | A | 8/1987 | Keller |
| 5,085,223 | A | 2/1992 | Lars et al. |
| RE35,648 | E | 11/1997 | Tenerz et al. |
| 5,715,827 | A | 2/1998 | Corl et al. |
| 6,112,598 | A | 9/2000 | Tenerz et al. |
| 6,167,763 | B1 | 1/2001 | Tenerz et al. |
| 2003/0028128 | A1 | 2/2003 | Tenerz |
| 2003/0040674 | A1 | 2/2003 | Corl et al. |

*Primary Examiner*—Edward Lefkowitz
*Assistant Examiner*—Andre Allen
(74) *Attorney, Agent, or Firm*—Foley & Lardner LLP

(57) ABSTRACT

A sensor and guide wire assembly (21; 31; 41) for intravascular measurements of physiological variables in a living body includes a core wire (22; 32; 42) and sensor element (23; 33; 43). The sensor element (23; 33; 43) includes basically a mounting base (24; 34; 44) and a pressure sensitive end portion (25; 35; 45) whose upper side is provided with a pressure sensitive device, such as a membrane (26; 36; 46). The mounting base (24; 34; 44) extends downwards from the end opposite to the pressure sensitive end (25; 35; 45), such that, when the sensor element (23; 33; 43) is mounted on the core wire (22; 32; 42), a clearance (27; 37; 47) is formed below the pressure sensitive end (25; 35; 45).

18 Claims, 4 Drawing Sheets

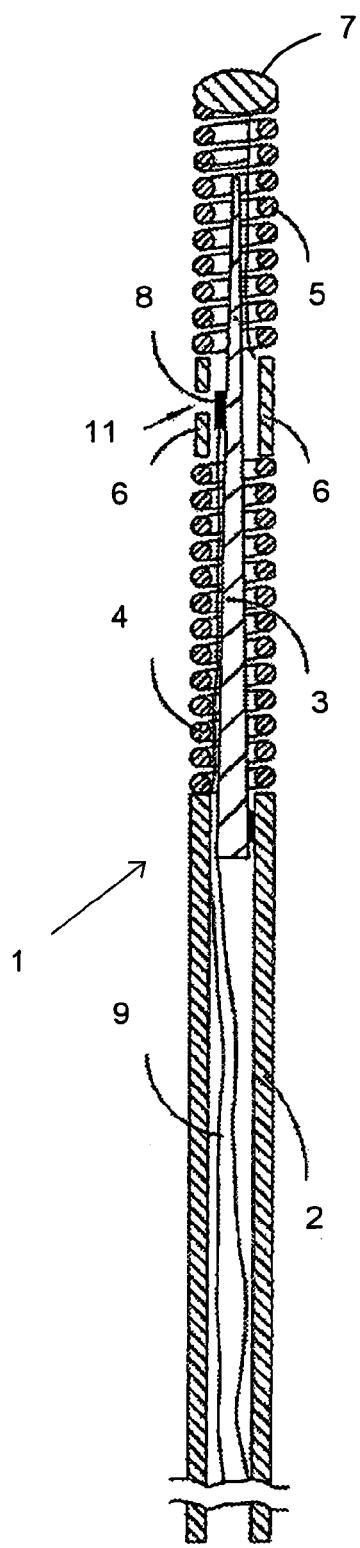
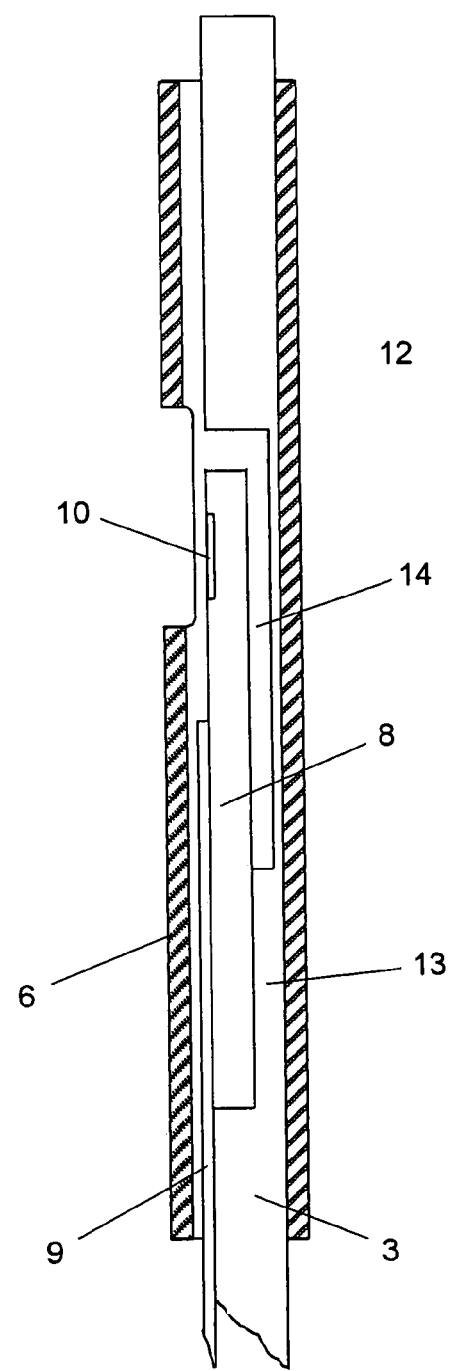
Fig. 1
(Prior Art)
Fig. 2
(Prior Art)

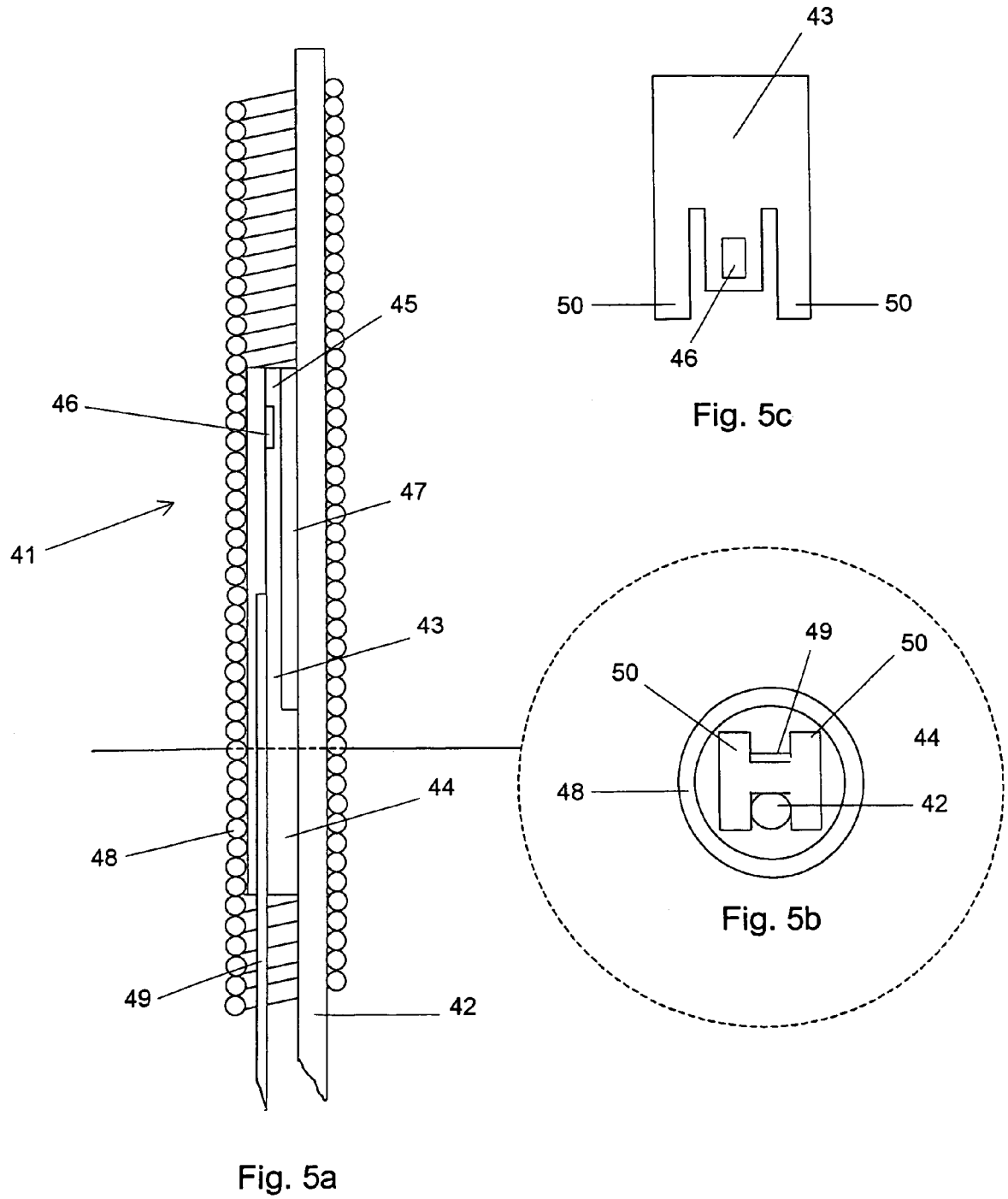

US 6,993,974 B2

SENSOR AND GUIDE WIRE ASSEMBLY

FIELD OF THE INVENTION

The present invention relates generally to sensor and guide wire assemblies, in which a sensor element is mounted at the distal end of a guide wire for intravascular measurements of physiological variables in a living body, and in particular to the shape and mounting arrangement of the sensor element.

BACKGROUND OF THE INVENTION

Sensor and guide wire assemblies in which a sensor is mounted at the distal end of a guide wire are known. In U.S. Pat. No. Re. 35,648, which is assigned to the present assignee, an example of such a sensor and guide wire assembly is disclosed, where a sensor guide comprises a sensor element, an electronic unit, a signal transmitting cable connecting the sensor element to the electronic unit, a flexible tube having the cable and the sensor element disposed therein, a solid metal wire, and a coil attached to the distal end of the solid wire. The sensor element comprises a pressure sensitive device, e.g. a membrane, with piezoresistive elements connected in a Wheatstone bridge-type of arrangement mounted thereon.

As is recognized in U.S. Pat. Nos. 6,112,598 and 6,167,763, which also are assigned to the present assignee, a potential problem with this kind of guide wire mounted sensors is the occurrence of so-called bending artefacts. A bending artefact is a change in the output signal from the sensor that is induced by a bending of the guide wire, rather than being induced by a change in the physical environment surrounding the sensor.

For a sensor and guide wire assembly like the one disclosed in U.S. Pat. No. Re. 35,648, this means that when the guide wire is bent, the bending of the guide wire imposes a strain on the sensor element, which thereby is deflected or stretched (or contracted). The deflection of the sensor element is then transferred to a deformation of the pressure sensitive device; and, according to well-known principles, the output from the Wheatstone bridge will thereby be affected by the bending of the guide wire.

According to U.S. Pat. Nos. 6,112,598 and 6,167,763, a solution to this problem is to mount the sensor element in a cantilevering fashion such that the pressure sensitive end of the sensor element does not contact any structure other than its mount. These two patents disclose several embodiments with different ways of mounting the sensor element so that bending forces are not exerted on the pressure sensitive end of the sensor element. A common feature of these embodiments is that an elongated, essentially rectangular sensor chip is mounted in a recess in the core wire in such a way that the proximal end of the chip is attached to the core wire, while the distal end of the sensor chip protrudes into the recess such that a clearance is provided below the distal portion of the chip where the pressure sensitive device (e.g. a membrane) is provided.

Although a sensor and guide wire assembly provided with a sensor chip designed and mounted according to the teachings of U.S. Pat. Nos. 6,112,598 and 6,167,763 in practise has proven to work well, the design of a sensor and guide wire assembly can be improved, not least from a manufacturing point of view.

SUMMARY OF THE INVENTION

As mentioned above, the sensor element according to the prior art comprises an elongated, essentially rectangular chip with a membrane made from polysilicon provided thereon. To achieve the desired resistance against bending artefacts, this chip can be mounted in different ways, the common feature being that it is the mounting arrangement—rather than the shape of the chip itself—that provides the desired resistance against bending artefacts.

An object of the present invention is to provide a new and improved design for a sensor chip so that, when the sensor chip is mounted in a sensor and guide wire assembly, the sensor and guide wire assembly will have the same or better characteristics regarding resistance against bending artefacts. Preferably, the sensor and guide wire assembly should at the same time be easier and thereby cheaper to manufacture.

These objects are achieved with a sensor chip and a sensor and guide wire assembly according to the present invention.

According to the invention, a sensor and guide wire assembly comprises a sensor element in the form of a generally rectangular and rather thin sensor chip with a pressure sensitive device provided thereon. The pressure sensitive device can be in the form of a membrane, which covers a small recess in the upper side at a first end of the sensor chip and which has piezoresistive elements mounted thereon. At its second and opposite end, the sensor chip is provided with a mounting base that extends downwards. The mounting base is adapted to be mounted on the surface of a core wire, which is a part of a sensor and guide wire assembly, such that the first end of the sensor chip is mounted in a cantilevering fashion, with a clearance being provided below the first end of the sensor chip where the pressure sensitive device is provided.

In one embodiment of a sensor chip according to the present invention, the mounting base is provided as an integrated part of the sensor chip, i.e. the sensor chip is manufactured in one piece, whereas another embodiment employs a sensor chip comprising a separate mounting base that is attached to the otherwise thin and flat structure of the sensor chip.

Another object of the present invention is to provide a method for manufacturing a sensor chip according to the present invention. In a first manufacturing process, the sensor chip is made from a single piece of silicon that is etched to the desired shape, including the mounting base. According to a second way of manufacturing, the sensor chip is produced by bonding a mounting base, which is made from silicon, to a silicon plate.

BRIEF DESCRIPTION OF THE DRAWINGS

FIG. 1 illustrates schematically the general design of a sensor and guide wire assembly according to the prior art.

FIG. 2 illustrates an example of a mounting arrangement for the sensor element of the sensor and guide wire assembly shown in FIG. 1.

FIG. 3a illustrates a portion of a first sensor and guide wire assembly comprising a sensor chip according to the present invention.

FIG. 3b is a cross-section of the sensor and guide wire assembly of FIG. 3a.

FIG. 4a illustrates a portion of a second sensor and guide wire assembly comprising a sensor chip according to the present invention.

FIG. 4b is a cross-section of the sensor and guide wire assembly of FIG. 4a.

FIG. 5a illustrates a portion of a third sensor and guide wire assembly comprising a sensor chip according to the present invention.

FIG. 5b is a cross-section of the sensor and guide wire assembly of FIG. 5a.

FIG. 5c is a plan view of the sensor chip of FIG. 5a.

DETAILED DESCRIPTION OF THE INVENTION

Figures 3A, 3B:
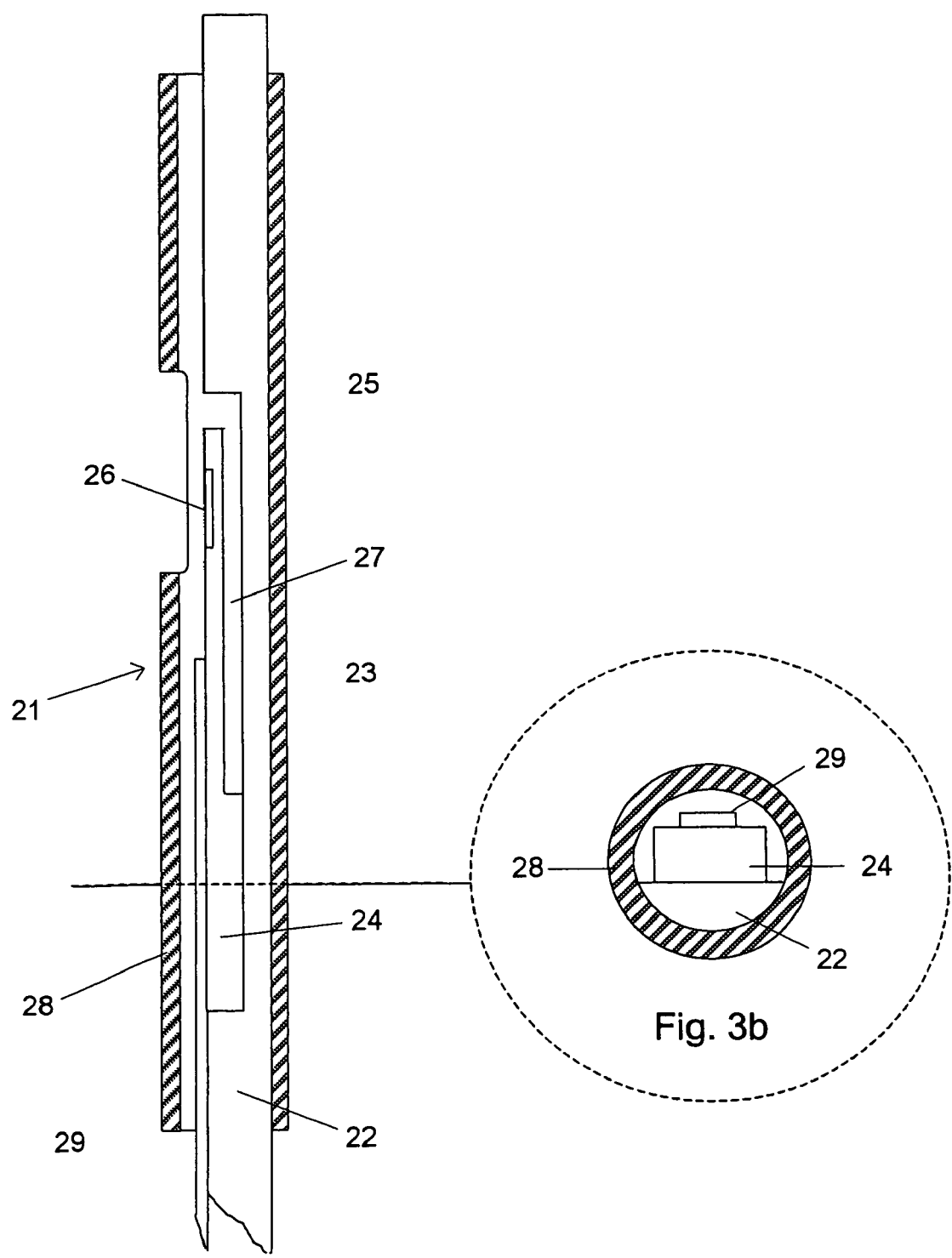

For better understanding of the context in which a sensor chip according to the present invention is going to be used, a sensor and guide wire assembly 1 of a conventional design is illustrated in FIG. 1. The sensor guide 1 comprises a hollow tube 2, a core wire 3, a first coil 4, a second coil 5, a jacket or sleeve 6, a dome-shaped tip 7, a sensor element or chip 8, and one or several electrical leads 9. The proximal end of the first coil 4 is attached to the distal end of the hollow tube 2, while the distal end of the first coil 4 is attached to the proximal end of the jacket 6. The proximal end of the second coil 5 is connected to the distal end of the jacket 6, and the dome-shaped tip 7 is attached to the distal end of the second coil 5. The core wire 3 is at least partly disposed inside the hollow tube 2 such that the distal portion of the core wire 3 extends out of the hollow tube 2 and into the second coil 5. The sensor element 8 is mounted on the core wire 3 at the position of the jacket 6, and is through the electrical leads 9 connected to an electronic unit (not shown in the figure). The sensor element 8 comprises a pressure sensitive device in the form of a membrane 10 (not visible in the figure), which through an aperture 11 in the jacket 6 is in contact with a medium, such as blood, surrounding the distal portion of the sensor guide 1.

Although not shown in the figure, the sensor element 8 further comprises an electrical circuitry, which in a Wheatstone bridge-type of arrangement is connected to one or several piezoresistive elements provided on the membrane 10. As is well known in the art, a certain pressure exerted on the membrane 10 from the surrounding medium will thereby correspond to a certain stretching of the membrane 10 and thereby to a certain resistance of the piezoresistive elements mounted thereon and, in turn, to a certain output from the sensor element 8. It should therefore be clear that it is highly preferable that this output from the sensor element 8 does not change due to factors that are not related to a real change in the physical properties of the surrounding medium. As was mentioned above, one such factor is so-called bending artefacts, the source of which is that a bending of the sensor guide 1 is transferred to a deformation of the membrane 10. Here, the discussion above about piezoresistive elements coupled in Wheatstone bridge-type of arrangement should only be seen as an illustrative exemplification; in short, the basic problem is that a pressure sensitive device, such as a membrane, can be influenced by a bending of a sensor guide.

To remedy the potentially adverse effects from bending artefacts, several different ways of mounting a sensor element are disclosed in U.S. Pat. Nos. 6,112,598 and 6,167,763, and in FIG. 2 one of these mounting arrangements is shown. FIG. 2 illustrates how the sensor chip 8, whose distal portion is provided with the membrane 10, is mounted on the core wire 3. The core wire 3 has been provided with a recess 12 that consists of two portions, a first portion having the purpose of a mounting shelf 13 for receiving the proximal portion of the chip 8 and a second portion 14, which is deeper than the first portion to allow the distal portion of the sensor chip 8 to protrude freely. The sensor chip 8 is thereby mounted in a cantilevering fashion, without the pressure sensitive distal end of the sensor chip 8 being in contact with any rigid structure. In this known design of a sensor guide, the sensor element 8 is disposed inside the jacket 6, and is through the electrical leads 9 in contact with an electronic unit (not shown in the figure).

For the mounting arrangement shown in FIG. 2, as well as for the other mounting arrangements according to the prior art, it is the mounting arrangement, including the design of the core wire, that provides the desired resistance against bending artefacts, while the sensor chip itself in all cases has the same generally rectangular and flat shape. In contrast, FIG. 3a shows a portion of a sensor and guide wire assembly 21 comprising a core wire 22 and sensor chip 23 according to the present invention. The sensor chip 23 comprises essentially two parts, a mounting base 24 and a pressure sensitive portion 25, on the upper side of which a pressure sensitive device in the form of a membrane 26 is provided. As an alternative, the pressure sensitive device could be arranged on the under side of the pressure sensitive portion 25. In the embodiment shown in FIG. 3a, the core wire 22 is provided with a recess in which the sensor chip 23 is mounted such that a clearance 27 is formed between the core wire 22 and the pressure sensitive portion 25 of the sensor chip 23. The recess in the core wire 22 can be made by grinding, spark machining or by laser machining, all methods well known to a person skilled in the art. FIG. 3b shows a cross-section of the sensor and guide wire assembly 21 of FIG. 3a. As can be seen from FIG. 3b, at the recess, the core wire 22 has a flat upper surface, which provides a comparatively large attachment area for the flat underside of the mounting base 24. The mounting base 24 can be attached to the core wire 22 by means of gluing. The sensor element 23 is disposed inside a jacket or sleeve 28, and is through at least one electrical lead 29 in contact with an electronic unit (not shown in the figures).

Figures 4A, 4B:
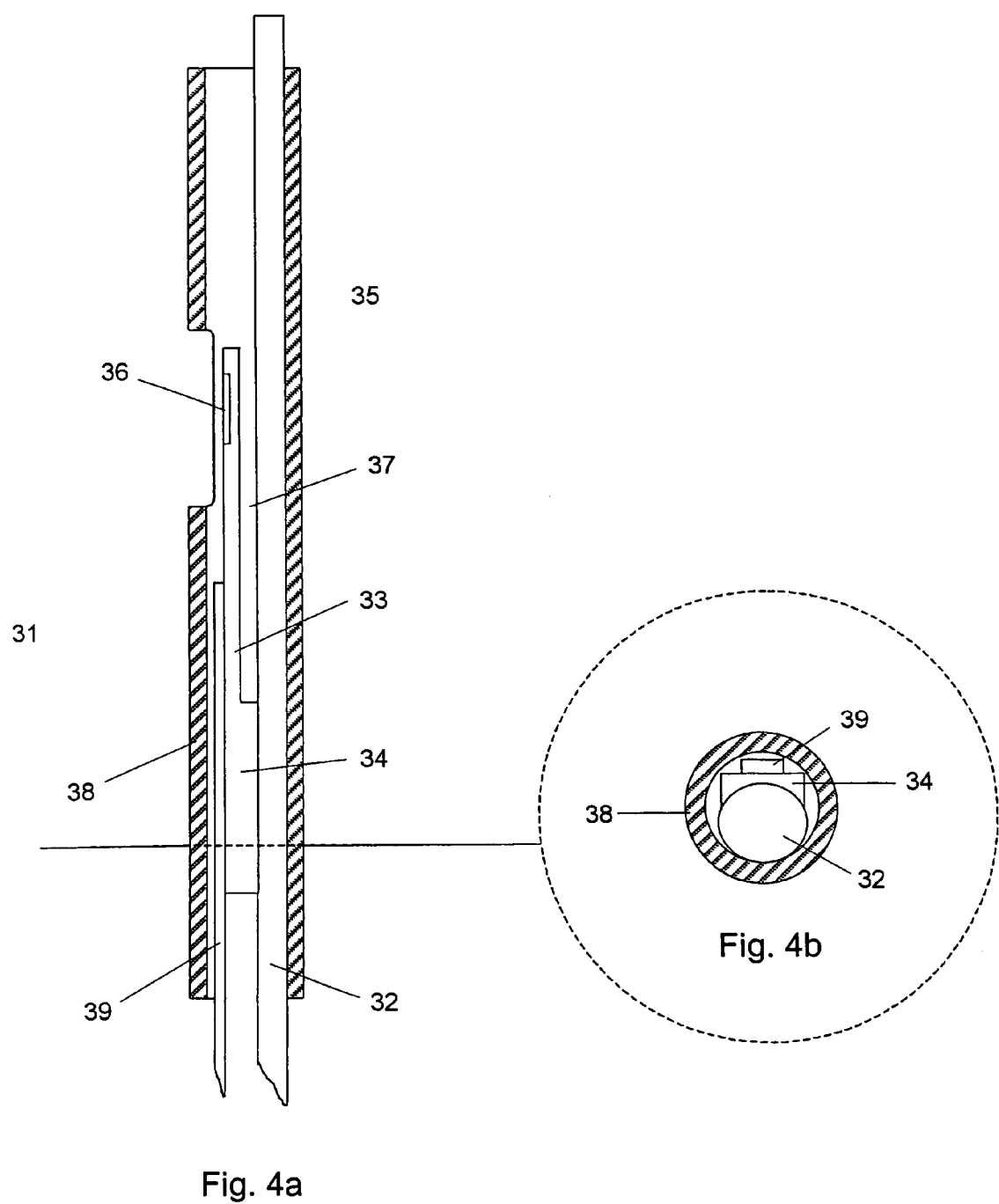

In FIG. 4a another way of mounting a sensor chip 33 according to the present invention is shown. The sensor chip 33 is mounted on a core wire 32 and is part of a sensor and guide wire assembly 31. Like the embodiment shown in FIG. 3a, the sensor chip 33 of FIG. 4a comprises essentially two parts, a mounting base 34 and a pressure sensitive end portion 35, on which a pressure sensitive device in the form of a membrane 36 is provided. The sensor guide 31 of FIG. 4a differs, however, from the sensor guide 21 of FIG. 3a in that the core wire 32 according to FIG. 4a lacks a recess. As is depicted in FIG. 4b, the core wire 32 has instead a circular cross-section, and the mounting base 34 of the sensor chip 33 is mounted on the circular outer surface of the core wire 32, such that a clearance 37 is formed between the core wire 32 and the pressure sensitive end 35 of the sensor chip 33. Further, FIG. 4b reveals that the underside of the mounting base 34 has been given a semi-circular shape, the curvature of which corresponds to the shape of the core wire 32. Apparently, by providing the mounting base 34 with such a semi-circular shape, a reliable mounting of the sensor chip 33 to the core wire 32 can be provided. It should, however, be noted that the strength of the mounting depends on the dimensions of the core wire and sensor chip as well as the way of mounting, e.g. the type of glue, and it may very well be that a reliable attachment of a sensor chip to a circular core wire can be provided also for a sensor chip whose mounting base has a flat underside. The sensor element 33 is also in this case disposed inside a jacket or sleeve 38, and is through at least one electrical lead 39 in contact with an electronic unit (not shown in the figures).

As mentioned several times before, a sensor chip according to the present invention differs from the sensor chips according to the prior art in that the present chip is provided with an extra structure in the form of a mounting base, whereas the sensor chips according to the prior art have a generally flat rectangular shape. This extra structure can, however, be extended to include more elaborated constructions, and in FIGS. 5a–c an example of such a design is illustrated. Here, a sensor chip 43 is mounted on a core wire 42 and is part of a sensor and guide wire assembly 41. Like the embodiments shown in FIGS. 3a–b and FIGS. 4a–b, respectively, the sensor chip 43 comprises a mounting base 44 and a pressure sensitive end portion 45, on which a pressure sensitive device in the form of a membrane 46 is provided. A clearance 47 is formed below the pressure sensitive end portion 45. In this embodiment, the sensor chip 43 is further provided with a protective structure 50 in the form of two extra elements 50. Each of these two extra elements 50 has a generally flat rectangular shape, and is arranged at a respective longitudinal edge of the sensor chip 43. As is best seen in FIG. 5b, the cross-section of the sensor chip 43 thereby assumes the shape of the letter H, with the extra elements 50 constituting the side-walls of the H. Further, FIG. 5c is a plan view of the sensor chip 43 and illustrates that at the pressure sensitive end portion 45 a small longitudinal gap is provided between a respective longitudinal edge of the sensor chip 43 and an adjacent side-wall 50. Also in this embodiment of the present invention the sensor chip 43 is thereby mounted in a cantilevering fashion. The extra elements or side-walls 50 of the sensor chip 43 can preferably extend beyond the pressure sensitive end portion 45 of the sensor chip 43. The purpose of these side-walls 50 will be apparent from the further description.

As is best seen in FIG. 5a, the sensor chip 43 is disposed inside a coil 48, i.e. the sensor guide 41 is not provided with a special protecting sleeve or jacket. A comparison with FIG. 1 reveals that the first and second coils, which extend on each side of the jacket or sleeve, thereby can be replaced with a single coil that extends from the hollow tube to the dome-shaped tip, which from a manufacturing point of view is advantageous. Especially from FIGS. 5a–b it is clear that the side-walls 50 constitute a protective structure 50 that provides essentially the same feature as a jacket or sleeve would do, i.e. the membrane 46 is protected from damages by the side-walls 50, and is through the coil 48 in contact with a medium surrounding the sensor guide 41. Here, it should further be noted that the upper portions of the extra elements 50, i.e. the portions extending away from the core wire 42, are more important than the lower portions of the extra elements 50 when it comes to protecting the membrane 46. For this reason, the lower portions of the H-shaped sensor chip could be eliminated such that a sensor chip instead is given a generally U-shaped cross-section. Also even more elaborated protective structures are conceivable, such as an O-shaped cross-section. The sensor element 43 is through at least one electrical lead 49 in contact with an electronic unit (not shown in the figures).

Further, although not shown in the figures, the sensor chips described above can comprise piezoresistive elements coupled in a Wheatstone bridge, with one part of the bridge being connected to the membrane and the other part of the bridge being connected to the chip surface outside the membrane. With such an arrangement, the sensor chip is a piezoresistive pressure transducer in that a certain pressure in the medium surrounding the sensor chip corresponds to a certain deformation of the membrane and, in turn, to a certain resistance of the Wheatstone bridge. The output signals from the pressure transducer will thereby reflect the pressure in the medium surrounding the sensor.

According to the above, a sensor chip according to the present invention comprises basically a mounting base and a pressure sensitive portion, on which a pressure sensitive device, e.g. a membrane, is provided. The sensor chips described in conjunction with FIGS. 3a–b and FIGS. 4a–b, respectively, have implicitly been assumed to have been made from a single piece of material (e.g. silicon), i.e. the mounting base is an integrated part of the sensor chip. Such a design of a silicon chip can be accomplished by means of etching. Another way of manufacturing a sensor chip is that a mounting base is attached to a flat structure. If the flat structure and the mounting base both are made from silicon, the joining can preferably be accomplished by means of bonding. The above applies also to the protective structure, which was exemplified as extra elements or side-walls and described in conjunction with FIGS. 5a–c, i.e. the protective structure can be an integrated part of the sensor chip, or the protective structure can be bonded to an otherwise flat and rectangular structure.

According to the invention a new design of a sensor chip is provided. The sensor chip is adapted to be mounted to a core wire, which is a part of a sensor and guide wire assembly. The invention relates thereby also to a new and improved design for a sensor and guide wire assembly, which has improved sensor chip characteristics especially regarding resistance against bending artefacts as well as mechanical strength and durability. With the new design of the sensor chip, the design of the core wire can be simplified, which, in turn, lowers the total production costs for the sensor and guide wire assembly as a whole.

Although the present invention has been described with reference to specific embodiments, also shown in the appended drawings, it will be apparent for those skilled in the art that many variations and modifications can be done within the scope of the invention as described in the specification and defined with reference to the claims below. It should in particular be noted that the improved characteristics of a sensor guide provided with a chip according to the invention are not dependent on the design of the other parts of the sensor guide. Therefore, a sensor and guide wire assembly may or may not include parts like jackets or sleeves, coils and tips with special shapes. Furthermore, the core wire, on which the sensor chip is mounted, may extend along essentially all the length of the sensor guide, or the core wire may only be provided at the distal portion of the sensor guide. Further, the core wire may be provided with recesses, grooves or other formations, which can facilitate the attachment of the sensor chip to the surface of the core wire; but also when such formations are provided, the essential feature of the present invention is that the sensor chip is provided with a mounting base that provides for a cantilevering mounting of the sensor chip, so that a clearance is provided below the pressure sensitive end of the sensor chip.

What is claimed is:

1. A sensor chip for a sensor guide wire assembly for intravascular measurements of at least one physiological variable in a living body, which sensor chip is adapted to be mounted on a core wire and has a first end portion, a first side of which is provided with a pressure sensitive device, wherein the sensor chip comprises a mounting base, which, at a second end of the sensor chip, extends downwards and is adapted for mounting to the core wire such that a clearance is formed between the first end portion and the core wire.

2. A sensor chip according to claim 1, wherein the mounting base is an integrated part of the sensor chip.

3. A sensor chip according to claim 1, wherein the mounting base is attached to the sensor chip.

4. A sensor chip according to claim 1, wherein the shape of an underside of the mounting base is adapted to the shape of the core wire.

5. A sensor chip according to claim 1, wherein the sensor chip further comprises a protective structure.

6. A sensor chip according to claim 5, wherein the protective structure is in the form of two extra elements, which are arranged such that the sensor chip has a H-or U-shaped cross-section.

7. A sensor chip according to claim 5, wherein the protective structure is an integrated part of the sensor chip.

8. A sensor chip according to claim 5, wherein the protective structure is attached to the sensor chip.

9. A sensor chip according to claim 1, wherein the sensor chip comprises a piezoresistive pressure transducer.

10. A sensor guide wire assembly for intravascular measurements of at least one physiological variable in a living body, comprising
a core wire and a sensor element having a first end portion, a first side of which is provided with a pressure sensitive device, wherein the sensor element has a mounting base, which, at a second end of the sensor element, extends downwards and is adapted for mounting to the core wire such that a clearance is formed between the first end portion and the core wire.

11. A sensor guide wire assembly according to claim 10, wherein the mounting base is an integrated part of the sensor element.

12. A sensor guide wire assembly according to claim 10, wherein the mounting base is attached to the sensor element.

13. A sensor guide wire assembly according to claim 10, wherein the shape of an underside of the mounting base is adapted to the shape of the core wire.

14. A sensor guide wire assembly according to claim 10, wherein the sensor element further comprises a protective structure.

15. A sensor guide wire assembly according to claim 14, wherein the protective structure is in the form of two extra elements, which are arranged such that the sensor element has a H- or U-shaped cross-section.

16. A sensor guide wire assembly according to claim 14, wherein the protective structure is an integrated part of the sensor element.

17. A sensor guide wire assembly according to claim 14, wherein the protective structure is attached to the sensor element.

18. A sensor guide wire assembly according to claim 10, wherein the sensor element comprises a piezoresistive pressure transducer.

* * * * *